US00PP16579P2

(12) United States Plant Patent
Koppe

(10) Patent No.: US PP16,579 P2
(45) Date of Patent: May 30, 2006

(54) ***BEGONIA* PLANT NAMED 'BINOS PINK'**

(50) Latin Name: *Begonia×hiemalis*
Varietal Denomination: Binos Pink

(75) Inventor: Lubbertus H. Koppe, Ermelo (NL)

(73) Assignee: Koppe Royalty B.V., Ermelo (NL)

( * ) Notice: Subject to any disclaimer, the term of this patent is extended or adjusted under 35 U.S.C. 154(b) by 121 days.

(21) Appl. No.: 11/050,878

(22) Filed: Feb. 5, 2005

(51) Int. Cl.
*A01H 5/00* (2006.01)

(52) U.S. Cl. ..... Plt./348
(58) Field of Classification Search ..... Plt./348
See application file for complete search history.

(56) References Cited

U.S. PATENT DOCUMENTS

PP3,772 P * 8/1975 Mikkelsen ..... Plt./348
PP5,158 P * 12/1983 Mikkelsen ..... Plt./348
PP5,321 P * 11/1984 Schelbeck ..... Plt./348
PP6,179 P * 5/1988 Hvid ..... Plt./348
PP12,598 P2 * 4/2002 Koppe ..... Plt./348
PP13,657 P2 * 3/2003 Koppe ..... Plt./348

OTHER PUBLICATIONS

UPOV ROM GTITM Computer Database, GTI Jouve Retrieval Software 2005/02 Citations for 'Binos Pink'.*

* cited by examiner

*Primary Examiner*—Kent Bell
*Assistant Examiner*—W. C. Haas
(74) *Attorney, Agent, or Firm*—C. A. Whealy

(57) ABSTRACT

A new and distinct cultivar of *Begonia* plant named 'Binos Pink', characterized by its upright and mounted plant habit; double flowers that are dark pink to light red in color and held above the foliage; and excellent postproduction longevity.

1 Drawing Sheet

Botanical designation: *Begonia×hiemalis.*
Cultivar denomination: 'Binos Pink'.

BACKGROUND OF THE INVENTION

The present Invention relates to a new and distinct cultivar of *Begonia* plant, botanically known as *Begonia×hiemalis*, commercially known as Elatior *Begonia*, and hereinafter referred to by the name 'Binos Pink'.

The new *Begonia* was discovered by the Inventor in a controlled environment in Ermelo, The Netherlands, in April, 2002, as a naturally-occurring whole plant mutation of *Begonia×hiemalis* cultivar Binos, disclosed in U.S. Plant Pat. No. 13,657. The new *Begonia* was observed as a single plant in a group of flowering plants of the parent cultivar. The selection of this plant was based on its flower coloration.

Asexual reproduction of the new *Begonia* by cuttings taken in a controlled environment in Ermelo, the Netherlands, has shown that the unique features of this new *Begonia* are stable and reproduced true to type in successive generations.

SUMMARY OF THE INVENTION

The cultivar 'Binos Pink' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Binos Pink'. These characteristics in combination distinguish 'Binos Pink' as a new and distinct *Begonia:*

1. Upright and mounded plant habit.
2. Double flowers that are dark pink to light red in color and held above the foliage.
3. Excellent postproduction longevity.

Plants of the new cultivar are most similar to plants of the parent, the cultivar Binos. Plants of the new cultivar differ primarily from plants of the cultivar Binos in flower color as plants of the cultivar Binos have darker red-colored flowers.

Compared to plants of the cultivar Binos Soft Pink, disclosed in U.S. Plant patent application Ser. No. 11/050,882, plants of the new *Begonia* have darker colored flowers than plants of the cultivar Binos Soft Pink.

BRIEF DESCRIPTION OF THE PHOTOGRAPHS

The accompanying colored photographs illustrate the overall appearance of the new *Begonia*, showing the colors as true as it is reasonably possible to obtain in colored reproductions of this type. Colors in the photographs may differ slightly from the coloe values cited in the detailed botanical description which accurately describe the colors of the new *Begonia.*

The photograph at the top of the sheet comprises a side perspective view of a typical flowering plant of 'Binos Pink'.

The photograph at the bottom of the sheet is a close up view of typical flowers and leaves of 'Binos Pink'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown in Ermelo, The Netherlands, under commercial practice in a glass-covered greenhouse. Average day and night temperature was about 20° C. during the first three to four weeks then lowered to an average day and night temperature of 19° C. until flowering. Four weeks after planting rooted cuttings in 14-cm containers, one week of long nyctoperiods of 16 hours was given followed by short nyctoperiods of eight hours until flowering. Plants used for the photographs and the description were about four months old.

Botanical classification: *Begonia×hiemalis* cultivar Binos Pink.

Commercial classification: Elatior *Begonia*.

Parentage: Naturally-occurring whole plant mutation of *Begonia×hiemalis* cultivar Binos, disclosed in U.S. Plant Pat. No. 13,657.

Propagation:

*Type*.—Cuttings.

*Time to develop roots*.—About 40 days at temperatures 20° C. to 22° C.

*Root description*.—Fine, fibrous, well-branched and spreading. Plants of the new *Begonia* have not been observed to form tubers.

Plant description:

*Plant form*.—Upright and mounded plant habit, inverted triangle; freely branching with good stem and stem base strength. Flowers are double and abundant. Plants flower continuously.

*Growth habit*.—Moderate growth rate, vigorous. Suitable for 12 to 15-cm containers. Under optimal environmental and cultural conditions, usually about four months are required to produce proportional 13-cm potted plants from cuttings. Vegetative shoots are formed at basal nodes and flowering shoots are formed at upper nodes.

*Plant height*.—About 25 to 30 cm.

*Plant width*.—About 40 cm.

*Leaves*.—Arrangement: Simple, alternate. Developing leaves, length: About 4 to 5 cm. Developing leaves, width: About 5.5 to 6 cm. Fully expanded leaves, length: About 10 to 14 cm. Fully expanded leaves, width: About 11 to 14 cm. Shape: Asymmetrically reniform. Apex: Acuminate. Base: Cordate. Margin: Doubly serrate. Texture, upper and lower surfaces: Smooth, glaborous. Venation pattern: Palmate. Color: Developing leaves, upper surface: 137A. Developing leaves, lower surface: 147B. Fully expanded leaves, upper surface: Darker than 147A. Fully expanded leaves, lower surface: 147B. Venation, upper and lower surfaces: 146D. Petiole length: About 1 to 6.5 cm. Petiole texture, upper and lower surfaces: Slightly pubescent. Petiole color, developing leaves, upper and lower surfaces: 152C. Petiole color, fully expanded leaves, upper and lower surfaces: 173A to 173C.

Flower description:

*Flowering habit*.—Double flowers with numerous tepals arranged in axillary cymes. Usually 9 to 12 flowers per cyme. Many cymes in flower simultaneously. Flowers positioned above the foliage. Flowering continuous.

*Natural flowering season*.—Plants will flower year round regardless of nyctoperiod, however plants flower earlier and more abundantly from mid-February until November in the Northern Hemisphere.

*Flowers*.—Shape: Rounded. Diameter: About 6.5 cm. Depth (height): About 2 cm.

*Flower buds*.—Length: About 1.2 to 2.2 cm. Diameter: About 1 to 1.8 cm. Color: 145C; towards the margin, 56A.

*Tepals*.—Arrangement: Rosette. Quantity per flower: Usually about 20 per flower. Size: Outer tepals: Length: About 3.5 to 3.8 cm. Width: About 4 to 4.5 cm. Inner tepals: Length: About 1.5 cm. Width: About 1.5 cm. Shape: Rounded flabellate. Apex: Rounded. Margin, outer and inner tepals: Slightly crenate. Texture, upper and lower surfaces: Smooth, glabrous; sanity. Color: When opening, upper surface: 53D towards the base, 4D. When opening, lower surface: 48B; towards the base, 145D. Fully opened, upper surface: Closest to 51A. Fully opened, lower surface: 48C; towards the margin, 54B.

*Flower bracts*.—Arrangement: Two, opposite. Shape: Broadly cordate. Apex: Apiculate. Margin: Serrate. Texture, upper and lower surfaces: Glabrous, smooth. Color, upper and lower surfaces: 146D.

*Peduncles*.—Angle: Erect. Length: About 1.5 to 6 cm. Texture: Slightly pubescent. Color: 145A.

*Pedicels*.—Angle: Erect. Length: About 2 to 3.8 cm. Texture: Smooth, glabrous. Color: 146D.

*Reproductive organs*.—Stamens: None observed. Pistils: None observed.

*Seed/fruit*.—Seed and fruit production have not been observed as reproductive organs are not formed.

Postproduction longevity:

*Individual flowers*.—Generally about two to three weeks.

*Whole plants*.—About six weeks under interior conditions.

Disease/pest resistance: Resistance to pathogens and pests common to *Begonia* has not been observed.

It is claimed:

1. A new and distinct cultivar of *Begonia* plant named 'Binos Pink', as illustrated and described.

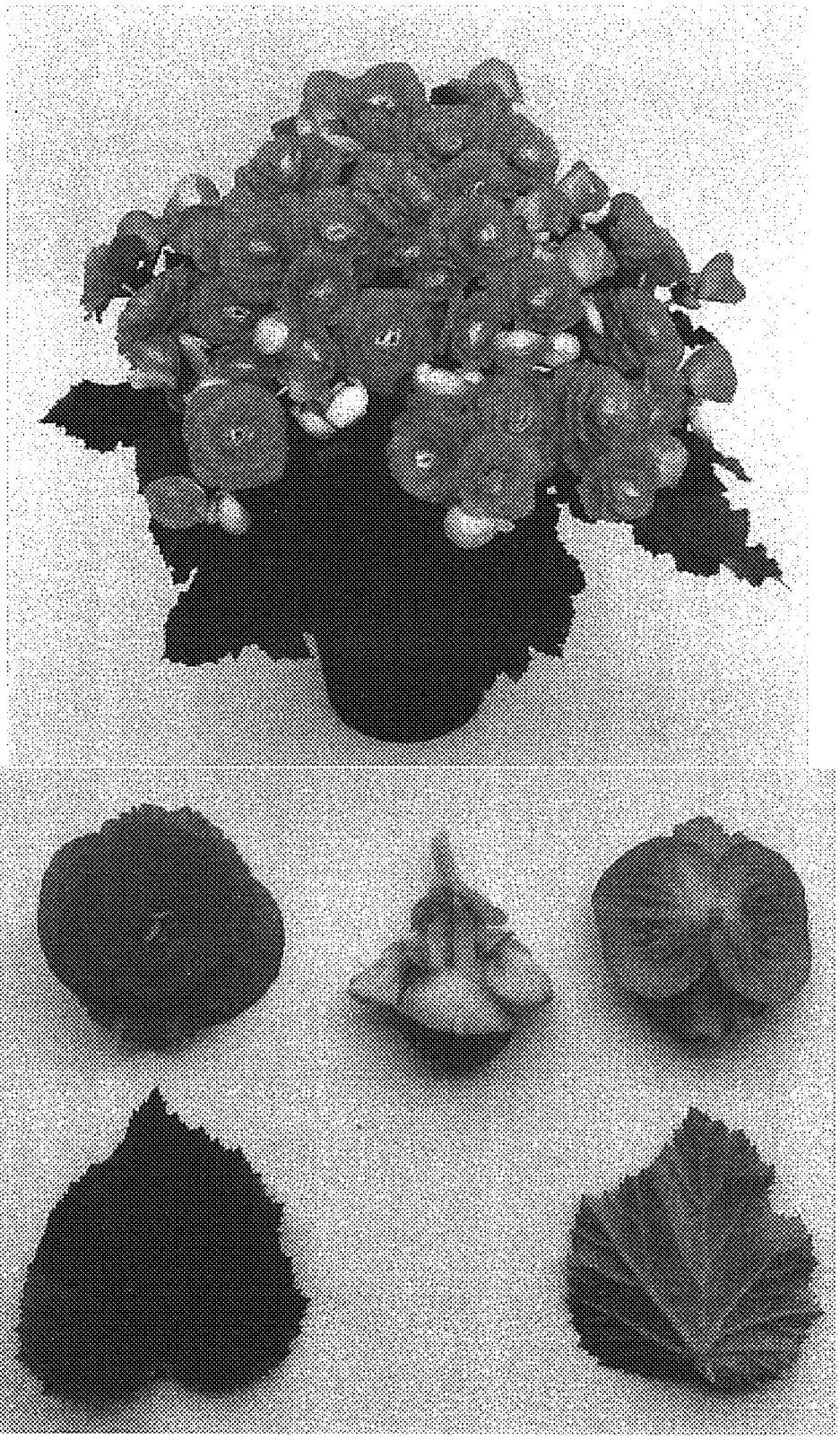

* * * * *